US012551316B2

(12) United States Patent
Eschborn

(10) Patent No.: US 12,551,316 B2
(45) Date of Patent: Feb. 17, 2026

(54) TRANSPORT TROLLEY FOR SURGICAL INSTRUMENTS

(71) Applicant: OLYMPUS Winter & Ibe GmbH, Hamburg (DE)

(72) Inventor: Sascha Eschborn, Ahrensburg (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 51 days.

(21) Appl. No.: 18/138,909

(22) Filed: Apr. 25, 2023

(65) Prior Publication Data

US 2023/0338112 A1 Oct. 26, 2023

Related U.S. Application Data

(60) Provisional application No. 63/334,743, filed on Apr. 26, 2022.

(51) Int. Cl.

| | |
|---|---|
| ***A61B 90/70*** | (2016.01) |
| ***A61B 50/13*** | (2016.01) |
| ***A61B 90/90*** | (2016.01) |
| ***B08B 9/032*** | (2006.01) |

(52) U.S. Cl.

CPC .............. *A61B 90/70* (2016.02); *A61B 50/13* (2016.02); *A61B 90/90* (2016.02); *B08B 9/032* (2013.01); *A61B 2090/701* (2016.02)

(58) Field of Classification Search

CPC ...................................................... A61B 90/70

See application file for complete search history.

(56) References Cited

U.S. PATENT DOCUMENTS

| | | | |
|---|---|---|---|
| 2014/0125482 A1 | 5/2014 | Rigsby et al. | |
| 2014/0166059 A1 | 6/2014 | Kosugi et al. | |

FOREIGN PATENT DOCUMENTS

| | | | |
|---|---|---|---|
| CN | 111317574 A * | 6/2020 | ............ A61B 50/13 |
| CN | 214712772 U | 11/2021 | |
| DE | 10 2005 048 211 A1 | 4/2007 | |
| DE | 10 2006 054 130 A1 | 7/2008 | |
| DE | 10 2017 202 869 A1 | 8/2018 | |
| DE | 10 2020 124 319 A1 | 3/2022 | |
| WO | 2012/044944 A2 | 4/2012 | |

OTHER PUBLICATIONS

Zhang et al., CN111317574, English machine translation, Jun. 2020 (Year: 2020).*

* cited by examiner

*Primary Examiner* — Jason Y Ko

(74) *Attorney, Agent, or Firm* — Scully, Scott, Murphy & Presser, P.C.

(57) ABSTRACT

A transport trolley including at least one receiving compartment configured to receive an instrument tray; and one or more of: a pre-cleaning device configured to pre-clean a surgical instrument in the instrument tray, the pre-cleaning device is configured to be connected to the surgical instrument by a coupling; and a pre-cleaning apparatus configured to pre-clean an outside of the surgical instrument.

17 Claims, 3 Drawing Sheets

TRANSPORT TROLLEY FOR SURGICAL INSTRUMENTS

CROSS-REFERENCE TO RELATED APPLICATION

The present application is based upon and claims the benefit of priority from U.S. Provisional Application No. 63/334,743 filed on Apr. 26, 2022, the entire contents of which is incorporated herein by reference.

BACKGROUND

Field

The present disclosure relates to a transport trolley for surgical instruments, such as endoscopes, and further relates to a surgical system. Moreover, the present disclosure relates to a method for cleaning a surgical instrument, such as an endoscope.

Prior Art

It is well known in the prior art that transport trolleys are used for the transport of endoscopes between an operation room and the room for reprocessing the endoscopes. After a surgery or a medical examination, the endoscopes are cleaned manually first and then disinfected or reprocessed automatically. In order to prevent residual dirt from drying in the endoscope channels and thus leading to blocked channels, the time between intervention and manual cleaning, as well as automated process, is limited. The manual cleaning of the surgical instruments is to be carried out typically within two hours. Moreover, the time between the manual cleaning and the automatic reprocessing of the surgical instruments shall not exceed approximately 30 minutes.

These time requirements for the manual cleaning and automatic reprocessing of surgical instruments entails personnel which must always be available to perform transport as well as manual and mechanical cleaning steps of the surgical instruments, such as when surgical instruments like endoscopes are used for surgeries at nights or on weekends.

SUMMARY

An object is to simplify or to improve the cleaning processes of surgical instruments significantly.

Such object can be solved by a transport trolley for surgical instruments, such as endoscopes, having at least one receiving compartment for receiving an instrument tray, such as a closable instrument tray, for arranging a surgical instrument in the instrument tray, and having a pre-cleaning device for a surgical instrument to be pre-cleaned which is arranged or can be arranged in the instrument tray, wherein the pre-cleaning device is connectable or connected to the surgical instrument to be pre-cleaned by a coupling device and/or having a pre-cleaning apparatus for pre-cleaning an outside of the surgical instrument.

The transport trolley can have at least one receiving compartment or several compartments for receiving an instrument tray with a surgical instrument positioned therein, wherein the surgical instrument in the instrument tray or in each info tray is pre-cleaned by a pre-cleaning device of the transport trolley, wherein the pre-cleaning device is connectable or connected with the surgical instrument in the instrument tray. After positioning the instrument tray with the surgical instrument in the corresponding receiving compartment and after a connection the pre-cleaning device with the surgical instrument, a pre-cleaning process of the surgical instrument, which can be automatic, can be carried out on the transport trolley.

The transport trolley can comprise several, for example three to six or more, receiving compartments for receiving an instrument tray with a surgical instrument. The surgical instrument itself can comprise at least one or more channels, which has or have to be pre-cleaned on the transport trolley. After positioning the instrument tray in the receiving compartment, the channels of the surgical instrument, such as an endoscope, can be connected or coupled with the pre-cleaning device by f one or more coupling devices, such as adapters. Further pre-cleaning process of the surgical instrument will be or is performed by activating the pre-cleaning device on the transport trolley. Therefore, the instrument tray can have a cover or the like in order to close the instrument tray for the pre-cleaning process.

In addition or as an alternative, the outside or the outer surfaces of the surgical instrument can be pre-cleaned by a pre-cleaning apparatus. Therefore, the external control knobs, control buttons or control wheels of the surgical instruments or the outside of the endoscope shaft or the like are pre-cleaned, wherein the surgical instrument is arranged in the instrument tray, which can be closed.

In addition, the transport trolley can be movable and comprises for example wheels or the like.

In order to perform the pre-cleaning of the surgical instrument in the instrument tray on the transport trolley, the pre-cleaning device can comprise a fluid supply for a pre-cleaning fluid for the surgical instrument and/or the pre-cleaning apparatus can comprise a fluid supply for a pre-cleaning fluid for the surgical instrument. The pre-cleaning fluid can be a pre-cleaning liquid and/or a pre-cleaning gel or a pre-cleaning gel-like mass or the like. By pumping the pre-cleaning liquid through one or more channels of the surgical instrument, the contamination of bacteria, dirt, such as visible dirt, or the like are reduced significantly.

The coupling device can be configured such that at least one channel or several channels of the surgical instrument is or are fluidically connected to the fluid supply for the pre-cleaning fluid. For example, by using the pre-cleaning fluid or liquid, the visible dirt as well as bacterial contamination can be reduced in such a way that the steps of a manual cleaning, such as on the transport trolley, before an automatic cleaning and disinfection process by a reprocessing device in a reprocessing room can be skipped. In addition, the pre-cleaned surgical instruments, such as endoscopes, can be stored on the transport trolley for a long time, which can lead to a considerable reduction in personnel for the reprocessing of surgical instruments.

The pre-cleaning device can comprise a fluid pump connected to the fluid supply by a fluid feed line. After connecting the pre-cleaning device with one or more channels of the surgical instrument via the coupling device, such as an adapter, the fluid pump pumps the pre-cleaning fluid from the fluid supply into the channels of the surgical instrument in order to remove the dirt or the bacteria inside the channels for the pre-cleaning process on the transport trolley.

In order to improve the pre-cleaning process on the transport trolley, a fluid return line can be provided for the pre-cleaning fluid emerging out or leaking from the surgical instrument. The fluid return line can be connected by a coupling device with the outlet of the channels of the surgical instrument. After flowing through the channels of the surgical instrument, the pre-cleaning fluid emerges out at the outlet side of the channels by flowing into the fluid return line and by discharging by the fluid return line.

In one embodiment of the transport trolley, the fluid return line can be connected to a fluid container for the pre-cleaning fluid and/or a filter for the precleaning fluid is arranged in the fluid return line and/or a pump is arranged in the fluid return line. Thereby, the used discharging pre-cleaning fluid is collected in the fluid container, wherein it is possible that the returning pre-cleaning fluid can be filtered. In addition, a pump can be arranged in the fluid return line, in order to pump the pre-cleaning fluid into the fluid container on the transport trolley. The pre-cleaning fluid or solution emerging e.g. out of the channels of the surgical instrument of from a distal end of the surgical instrument can be collected and can be recycled by a filter system in a further embodiment so that recycled fluid can be (re)used for flushing or pre-cleaning the surgical instruments for a longer term.

The fluid return line can be configured in such a way that the fluid return line can be coupled or is coupled to at least one channel or several channels of the surgical instrument, such as by an adapter.

Moreover, the fluid container can be fluidically connected to the fluid supply by a fluid line, wherein a filter for the pre-cleaning fluid and/or a pump for the pre-cleaning fluid can be provided in the fluid line.

The transport trolley can be provided with an identification sensor for detecting an identification code provided on the surgical instrument, such as the instrument to be pre-cleaned. By the identification sensor, the surgical instrument to be cleaned or pre-cleaned in the tray can be easily identified and recorded for the whole cleaning process. Thereby, it is recorded which surgical endoscope is positioned in the instrument tray.

The identification sensor can be configured as a scanner or as a barcode scanner or as an RFID sensor (radio frequency identification sensor). In this context, the instrument tray and/or the surgical instrument can be provided with an identification tag or the like or with a barcode or a RFID tag.

It is also provided in one embodiment of the transport trolley that the pre-cleaning device can comprise a controller for controlling at least one pre-cleaning process for pre-cleaning the surgical instrument on the transport trolley. The controller is configured to enable a pre-cleaning process, which can be automatic, of the surgical instruments on the transport trolley before the reprocessing process by a cleaning and disinfection reprocessing device in a reprocessing room or area.

Furthermore, the pre-cleaning device can be configured to pre-clean at least one channel or several channels of the surgical instrument by the pre-cleaning fluid, such as in a pre-cleaning process.

The pre-cleaning apparatus can comprise a nozzle and/or an outlet port, wherein the nozzle and/or the outlet port are arranged in the instrument tray. Thereby, the outer surface or the outside as well as the outer control knobs, control buttons or control wheels are pre-cleaned by the pre-cleaning fluid in contact with the outside of the instrument.

The pre-cleaning apparatus can comprise a fluid supply for a pre-cleaning fluid for pre-cleaning the outside of the surgical instrument. The fluid supply for the pre-cleaning apparatus can be different from the fluid supply for the pre-cleaning device. In one embodiment, the pre-cleaning fluid can be provided in one common fluid supply for the pre-cleaning apparatus and the pre-cleaning device.

The pre-cleaning apparatus can comprise a fluid pump connected to the fluid supply by a fluid feed line. In this context, the pre-cleaning apparatus and the pre-cleaning device can have the same fluid pump or separate fluid pumps.

A fluid outlet line can be provided for the pre-cleaning fluid emerging out or leaking from the instrument tray. Thereby, the pre-cleaning fluid for the pre-cleaning of the outside of the surgical instruments can flow or can be discharged out of the instrument tray, which can be closed, after pre-cleaning the outside of the surgical instrument.

The fluid outlet line can be connected to a fluid container for the pre-cleaning fluid and/or a filter for the pre-cleaning fluid can be arranged in the fluid outlet line and/or a pump can be arranged in the fluid outlet line.

In addition, such object can be solved by a surgical system comprising a transport trolley as described above. In this context, reference is expressly made accordingly to the embodiments as described above.

Such object can also be achieved by a method for cleaning a surgical instrument, such as an endoscope, using a transport trolley, as described above, wherein a pre-cleaning of the surgical instrument, which can be automatic, of at least one or more channels of the surgical instrument can be carried out.

Furthermore, after the pre-cleaning of the surgical instrument by the pre-cleaning device of the transport trolley, the surgical instrument can be processed by processing device, which can be stationary. To avoid repetitions, reference is expressly made to the above embodiments.

BRIEF DESCRIPTION OF THE DRAWINGS

Further features will become evident from the description of embodiments, together with the claims and the appended drawings. Embodiments can fulfill individual features or a combination of several features.

The embodiments are described below, without restricting the general idea of the invention, based on the exemplary embodiments in reference to the drawings, whereby we expressly refer to the drawings with regard to the disclosure of all details that are not explained in greater detail in the text. In the drawings.

DETAILED DESCRIPTION

Figure 1:
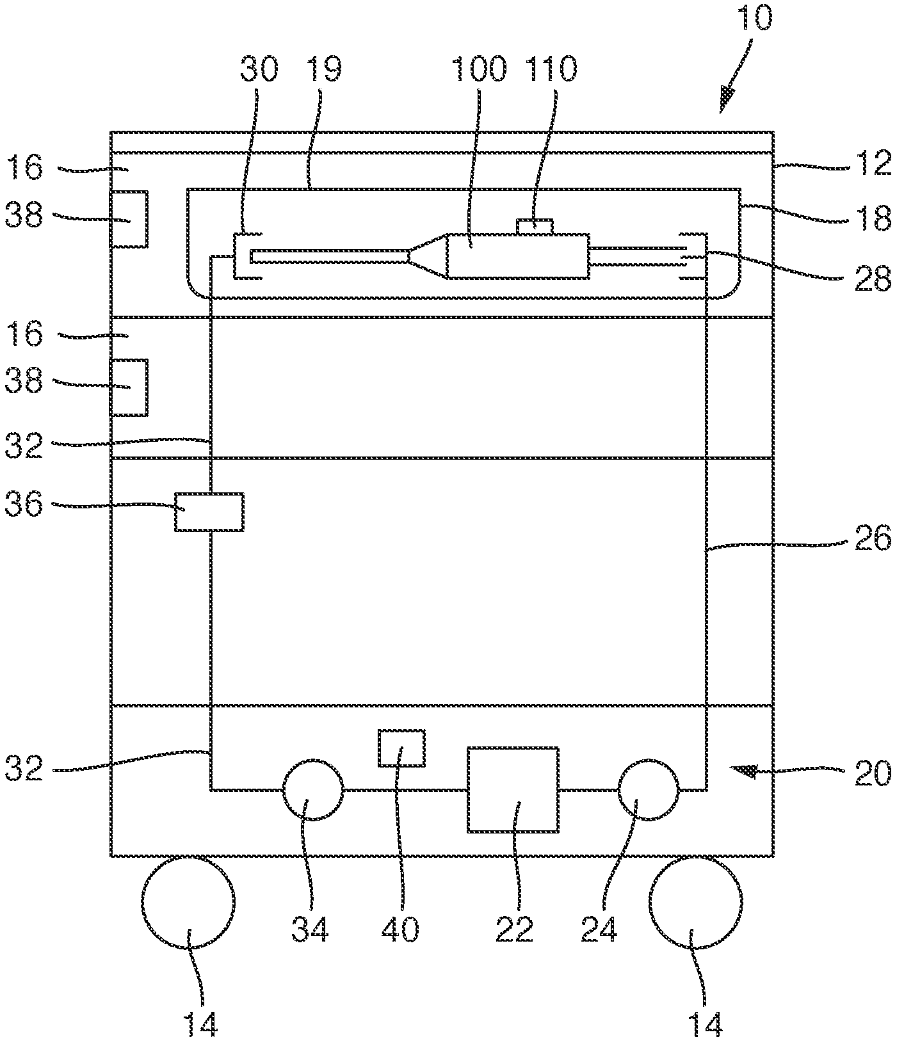
FIG. 1 illustrates a schematic cross-sectional representation of a transport trolley for surgical instruments.

In the drawings, the same or similar elements and/or parts are, in each case, provided with the same reference numerals such that they are not introduced again in each case.

In FIG. 1 shows, in a schematic cross-section view, a mobile transport trolley 10 for surgical instruments 100, such as endoscopes. The mobile transport trolley 10 comprises a rack 12 with wheels 14 at the bottom. The rack 12 is provided with receiving compartments 16 for receiving an instrument tray 18 (one of which is illustrated in FIG. 1). In the instrument tray 18, one surgical instrument 100 is arranged after the use of the surgical instrument, for example for a surgery.

The instrument tray 18 comprises a pivotable, cover 19, which can be pivotable, in order to close the instrument tray after accommodating the surgical instrument 100 inside the instrument tray 18. The closed instrument tray 18 is positioned in the receiving compartment 16 for pre-cleaning the surgical instrument on the transport trolley 10.

Moreover, the transport trolley 10 comprises a pre-cleaning device 20 for the pre-cleaning process of the surgical instrument 100. The pre-cleaning device 20 has a fluid supply 22, which is filled with a pre-cleaning fluid or liquid for the surgical instrument 100. The fluid supply 22 is connected with the surgical instrument 100 via a pump 24, wherein the pump 24 is connected with the surgical instrument by a fluid feed line 26. At the end of the fluid feed line 26 an adapter 28 or connector is provided in order to connect one or more channels (hereinafter channels) of the surgical instrument to the fluid feed line 26.

The pump 24 pumps the pre-cleaning fluid from the fluid supply 22 into the channels of the surgical instrument 100. The pre-cleaning fluid emerges out of the channels of the surgical instrument 100 at the outlet side of the channels. At the outlet side of the channels a connector 30 is provided in order to connect the outlet side of the channels of the surgical instrument with a fluid return line 32. The emerging pre-cleaning fluid flows or is discharged through the fluid return line 32 and is pumped by a pump 34 in the fluid return line 32 into the fluid supply 22. In the fluid return line 32 a filter 36 is provided in order to filter the unclean returned or discharged pre-cleaning fluid.

Furthermore, the rack 12 of the transport trolley 10 has an identification sensor 38 or the like corresponding to each receiving compartment 16 in order to identify the surgical instrument 100, which has to be pre-cleaned on the transport trolley 10. Therefore, the surgical instruments 100 are provided with an RFID tag 110. The information provided by the RFID tag can be read by the identification sensor 38.

In addition, the transport trolley 10 comprises a controller 40 configured to control the pre-cleaning processes of the surgical instrument 100 by the pre-cleaning device 20 arranged on the transport trolley 10. The controller can be hardware or any combination of hardware and software and also have a corresponding memory.

In a further (non-shown) embodiment, the fluid return line 32 can be connected with a separated fluid container in order to collect the pre-cleaning fluid emerging out of the channels of the surgical instrument 100.

The transport trolley 100 is used for a pre-cleaning process of the surgical instruments 100, wherein the used surgical instruments are accommodated in the receiving compartments 16 of the transport trolley 10 for pre-cleaning the surgical instruments, before the pre-cleaned surgical instruments are transported or moved to a reprocessing and disinfection device, which can be stationary.

Figure 2A:
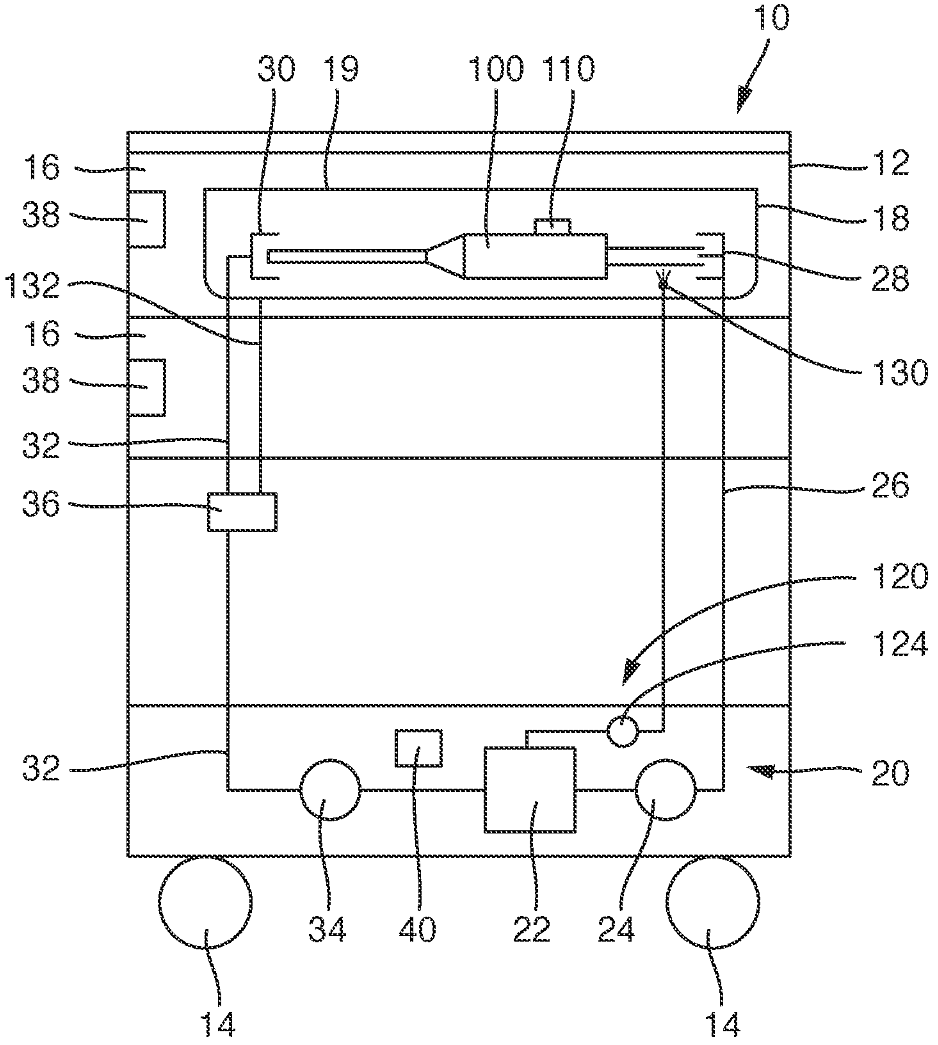
FIG. 2*a* illustrates a schematic cross-sectional representation of a transport trolley for surgical instruments according to another embodiment.
Figure 2B:
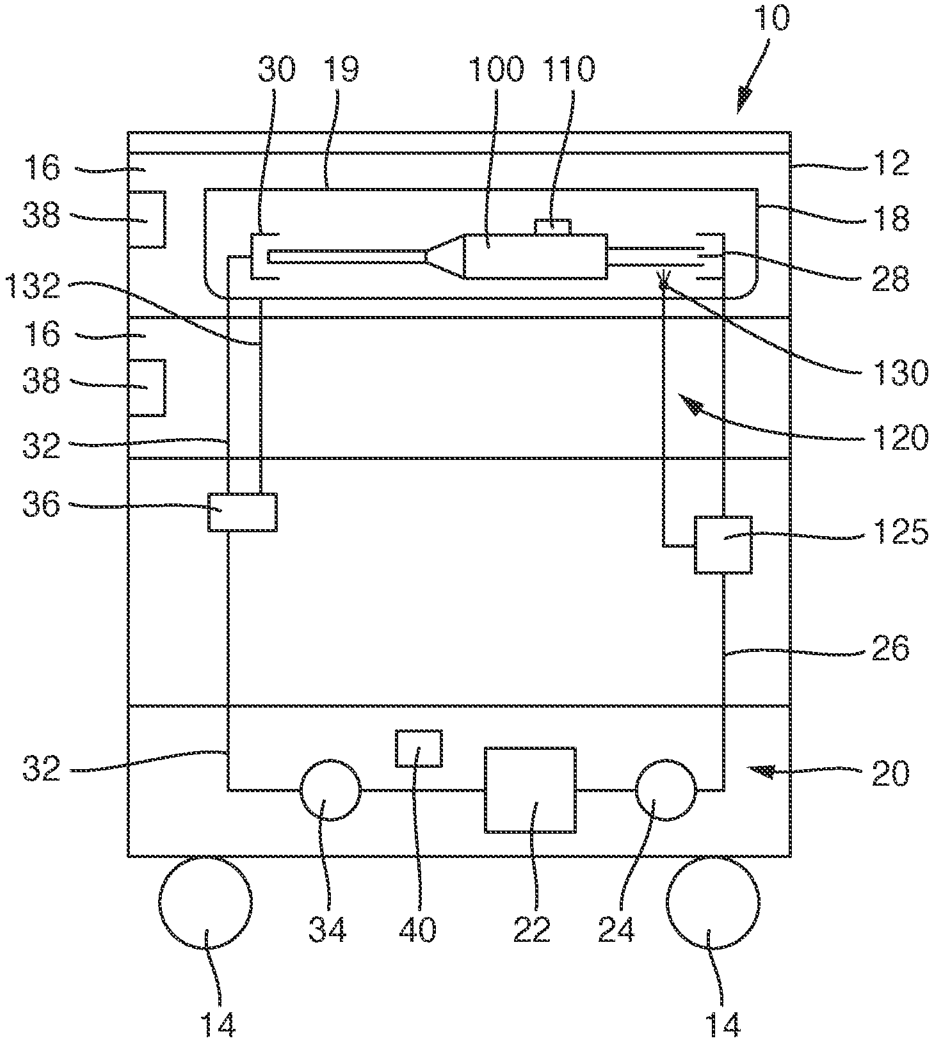
FIG. 2*b* illustrates a schematic cross-sectional representation of a transport trolley for surgical instruments according to another embodiment.

The embodiments shown in FIG. 2*a* and FIG. 2*b* illustrate each schematically of a transport trolley for surgical instruments in cross-section. In comparison to the embodiment of FIG. 1, the transport trolley 10 in FIG. 2*a* comprises a pre-cleaning apparatus 120 for the pre-cleaning of the outside of the surgical instrument 100, wherein a pump 124 is connected with the fluid supply 22 in order to pump or to convey a pre-cleaning fluid to a nozzle 130, which sprays the pre-cleaning fluid onto the outer surface of the surgical instrument 100 in the instrument tray 18. Hereby, the outer surface as well as outer operating units, such as control knobs, buttons and/or wheels etc., of the surgical instrument 100 are pre-cleaned by the pre-cleaning fluid. The pre-cleaning fluid for the outer surface of the surgical instrument is discharged out of the instrument tray by the fluid outlet line 132.

According to the embodiment of FIG. 2*b*, the fluid supply 22 is connected via one common pump 24 and a valve 125 with the adapter 28. Moreover, the valve 125 in the feed line 26 is also connected with the nozzle 130 in order to pre-clean the outside of the surgical instruments 100. Depending on the switching or the position of the valve 125, the inner channels of the surgical instrument 100 and/or the outside of the surgical instrument 100 is pre-cleaned by the pre-cleaning fluid.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES

10 Transport trolley
12 Rack
14 Wheel
16 Receiving compartment
18 Instrument tray
19 Cover
20 Pre-cleaning device
22 Fluid supply
24 Pump
26 Fluid feed line
28 Adapter
30 Connector
32 Fluid return line
34 Pump
36 Filter
38 Identification sensor
40 Control unit
100 Surgical instrument
110 RFID tag
120 Pre-cleaning device
124 Pump
125 Valve
130 Nozzle
132 Fluid outlet line

What is claimed is:

1. A mobile transport trolley for pre-cleaning a surgical instrument prior to cleaning the surgical instrument with a reprocessing device, the mobile transport trolley comprising:

at least one receiving compartment configured to receive an instrument tray; and a pre-cleaning device configured to pre-clean one or more internal channels of a surgical instrument in the instrument tray, the pre-cleaning device having a fluid feed line, the fluid feed line having an adapter at an end thereof, the adapter being configured to be connected to the one or more internal channels of the surgical instrument to provide a pre-cleaning fluid supply to the one or more internal channels.

2. The mobile transport trolley according to claim 1, further comprising a fluid supply configured to hold the pre-cleaning fluid for use with the pre-cleaning device.

3. The mobile transport trolley according to claim 2, wherein the adapter is configured to fluidly connect the one or more internal channels of the surgical instrument to the pre-cleaning fluid in the fluid supply.

4. The mobile transport trolley according to claim 2, further comprising a fluid pump connected to the fluid supply by a fluid feed line.

5. The mobile transport trolley according to claim 2, further comprising a fluid return line for removing the pre-cleaning fluid from the instrument tray.

6. The mobile transport trolley according to claim 5, wherein the fluid return line is connected to the fluid supply configured to hold the pre-cleaning fluid and one or more of a filter for the pre-cleaning fluid is arranged in the fluid return line and a pump is arranged in the fluid return line.

7. The mobile transport trolley according to claim 5, wherein the fluid return line is coupled to the one or more internal channels of the surgical instrument.

8. The mobile transport trolley according to claim 1, further comprising an identification sensor configured to detect an identification code provided on the surgical instrument.

9. The mobile transport trolley according to claim 8, wherein the identification sensor is selected from a list consisting of a scanner, a barcode scanner and an RFID sensor.

10. The mobile transport trolley according to claim 1, further comprising a controller configured to control at least one pre-cleaning process for pre-cleaning the surgical instrument.

11. The mobile transport trolley according to claim 1, further comprising a pre-cleaning apparatus configured to pre-clean an exterior of the surgical instrument.

12. A mobile transport trolley for pre-cleaning a surgical instrument prior to cleaning the surgical instrument with a reprocessing device, the mobile transport trolley comprising:

at least one receiving compartment configured to receive an instrument tray; and a first pre-cleaning apparatus configured to pre-clean an exterior of the surgical instrument; and a second pre-cleaning device configured to pre-clean one or more internal channels of the surgical instrument in the instrument tray, the second pre-cleaning device having a fluid feed line, the fluid feed line having an adapter at an end thereof, the adapter being configured to be connected to the one or more internal channels of the surgical instrument to provide a pre-cleaning fluid supply to the one or more internal channels.

13. The mobile transport trolley according to claim 11, wherein the pre-cleaning apparatus comprises one or more of a nozzle and an outlet port, wherein one or more of the nozzle and the outlet port are arranged in the instrument tray.

14. The mobile transport trolley according to claim 11, wherein the pre-cleaning apparatus comprises a fluid supply configured to hold the pre-cleaning fluid for pre-cleaning the exterior of the surgical instrument.

15. The mobile transport trolley according to claim 11, wherein the pre-cleaning apparatus comprises a fluid pump connected to the fluid supply by a fluid feed line.

16. The mobile transport trolley according to claim 11, further comprising a fluid outlet line configured to remove the pre-cleaning fluid from the instrument tray.

17. The mobile transport trolley according to claim 16, wherein the fluid outlet line is connected to a fluid container configured to hold the pre-cleaning fluid and one or more of a filter for the pre-cleaning fluid is arranged in the fluid outlet line and a pump is arranged in the fluid outlet line.

* * * * *